US009835435B2

(12) United States Patent
Knüttel

(10) Patent No.: US 9,835,435 B2
(45) Date of Patent: Dec. 5, 2017

(54) APPARATUS FOR DETECTING A 3D STRUCTURE OF AN OBJECT

(71) Applicant: Voco GmbH, Cuxhaven (DE)

(72) Inventor: Alexander Knüttel, Viernheim (DE)

(73) Assignee: Voco GmbH, Cuxhaven (DE)

(*) Notice: Subject to any disclaimer, the term of this patent is extended or adjusted under 35 U.S.C. 154(b) by 153 days.

(21) Appl. No.: 14/717,282

(22) Filed: May 20, 2015

(65) Prior Publication Data
US 2015/0338209 A1    Nov. 26, 2015

(30) Foreign Application Priority Data

May 23, 2014  (EP) .................................... 14169576

(51) Int. Cl.
*G01B 11/02* (2006.01)
*G01B 9/02* (2006.01)
(Continued)

(52) U.S. Cl.
CPC ........ *G01B 9/02029* (2013.01); *A61C 9/0073* (2013.01); *A61C 13/082* (2013.01);
(Continued)

(58) Field of Classification Search
CPC ............ G01B 9/02029; G01B 9/02027; G01B 9/02007; G01B 9/02047; G01B 9/02091;
(Continued)

(56) References Cited

U.S. PATENT DOCUMENTS

| 2005/0283065 A1* | 12/2005 | Babayoff | A61B 1/00009 |
| | | | 600/407 |
| 2007/0134615 A1* | 6/2007 | Lovely | A61B 5/0088 |
| | | | 433/29 |

(Continued)

FOREIGN PATENT DOCUMENTS

EP    2 796 938 A1    10/2014

OTHER PUBLICATIONS

Feng, et al., Single-exposure Color Digital Holography, Holography, Diffractive Optics, and Applications IV, Proc. of SPIE vol. 7848, 784826-1 to 784826-6.

*Primary Examiner* — Tarifur Chowdhury
*Assistant Examiner* — Jonathon Cook
(74) *Attorney, Agent, or Firm* — Bose McKinney & Evans LLP

(57) ABSTRACT

Apparatus for detecting a 3D structure of an object, comprising at least three laser emitters and a beam splitter that splits the laser radiation of the laser emitters into a reference radiation and an illumination radiation. The illumination radiation strikes the object to be measured, is reflected by the object as object radiation and interferes with the reference radiation. A detector receives the interference patterns formed from the interference of the reference and object radiation and an analysis unit analyzes the interference patterns. At least two of the laser emitters emit laser radiation in the invisible range and the analysis unit detects the object in three dimensions based on the interference patterns of the invisible laser radiation. At least one of the laser
(Continued)

emitters emits colored laser radiation and the analysis unit deduces the object's color based on the intensity of the colored object radiation reflected by the object.

16 Claims, 2 Drawing Sheets

(51) Int. Cl.
  *A61C 13/08* (2006.01)
  *G01J 3/50* (2006.01)
  *G01B 11/24* (2006.01)
  *A61C 9/00* (2006.01)
  *G03H 1/04* (2006.01)
  *G03H 1/00* (2006.01)

(52) U.S. Cl.
  CPC ..... *G01B 9/02007* (2013.01); *G01B 9/02027* (2013.01); *G01B 9/02047* (2013.01); *G01B 11/2441* (2013.01); *G01J 3/508* (2013.01); *G03H 1/0443* (2013.01); *G03H 1/0465* (2013.01); *G03H 2001/0033* (2013.01); *G03H 2210/13* (2013.01); *G03H 2210/30* (2013.01); *G03H 2222/13* (2013.01); *G03H 2222/16* (2013.01); *G03H 2222/34* (2013.01)

(58) Field of Classification Search
  CPC ......... G01B 11/2441; G01J 3/46; G01J 3/508; A61C 9/0073; A61C 13/082; G03H 1/0443; G03H 1/0465; G03H 2001/0033; G03H 2210/13; G03H 2210/30; G03H 2222/13; G03H 2222/16; G03H 2222/18; G03H 2222/34
  USPC .................................................. 356/511, 407
  See application file for complete search history.

(56) References Cited

U.S. PATENT DOCUMENTS

| | | | |
|---|---|---|---|
| 2008/0063998 A1* | 3/2008 | Liang | A61B 1/0638 433/29 |
| 2011/0292402 A1 | 12/2011 | Awatsuji et al. | |
| 2013/0302746 A1 | 11/2013 | Liang et al. | |
| 2014/0320865 A1 | 10/2014 | Knüttel | |

* cited by examiner

APPARATUS FOR DETECTING A 3D STRUCTURE OF AN OBJECT

RELATED APPLICATIONS

This application claims priority to EP 14 169 576.7, filed May 23, 2014, the entire disclosure of which is hereby incorporated herein by reference.

BACKGROUND

The present invention relates to an apparatus for detecting a 3D structure of an object comprising at least three laser emitters, optical devices, a detector and an analysis unit.

Laser emitters each generate laser radiation with a wavelength in such a manner that the wavelengths of the emitted laser radiation differ from one another. At least two of the laser emitters emit laser radiation in the invisible range. At least one of the optical devices is a beam splitter, which splits the laser radiation of the laser emitters into a reference radiation and an illumination radiation in such a manner that the illumination radiation strikes the object to be measured, is reflected by the object as object radiation and interferes with the reference radiation. The detector receives the interference pattern formed due to the interference of the reference radiation and the object radiation. The analysis unit is connected to the detector and serves to analyze the interference pattern received. The analysis unit is designed to detect the object in three dimensions based on the interference patterns of the invisible laser radiation.

Such apparatuses are used in dentistry, for example. They are used to detect objects such as a tooth, parts of a jaw or a complete jawbone in three dimensions. The dimensions required for producing models of the bite and the jaw can thus be detected without contact. This completely eliminates the task of taking impressions directly on the patient.

EP 2796938 discloses such an apparatus. It operates according to the principle of digital holography. The apparatus comprises at least two laser emitters, which emit laser radiation at different wavelengths. The laser radiation of each laser emitter is divided into reference radiation and object radiation with the help of a beam splitter. Whereas the reference radiation is deflected to a detector by means of a mirror arrangement, the illumination radiation strikes the object to be detected, is reflected by it as object radiation and is also sent to the detector. The reference radiation and object radiation with an identical wavelength interfere with one another. The resulting reference patterns are received by the detector. The three-dimensional structure of the object to be measured can be detected on the basis of interference patterns formed by laser radiation from different laser emitters. However, the color of the object cannot be detected because light from the near-infrared range is preferably used.

SUMMARY

This disclosure provides an apparatus for detecting a 3D structure of an object with which the color of the object to be detected can be determined.

At least one of the laser emitters is a color laser, which emits colored laser radiation. The analysis unit is designed to determine the color of the object on the basis of the intensity of the colored object radiation reflected by the object. This is done by the fact that the at least one color component of the object, which corresponds to the color of the colored laser radiation, is detected by means of the analysis unit. The wavelength of the reflected object radiation is thus the same as the wavelength of the detected color component of the object. For example, if the color laser emits blue laser radiation and if the intensity of the reflected blue object radiation is approximately 100%, it is recognized that the object to be measured has a blue color. If using a plurality of color lasers having different types of colored laser radiation, then different color components of the object are detected according to the number of color lasers. By combining the individual color components, it is then possible to deduce the color of the object and/or it can be determined. The more color lasers are used, the higher is the accuracy in determination of the object color.

On their path in the direction of the detector, the colored reference radiation and object radiation of the color laser interfere with one another. The position of the object point, from which the object radiation was reflected in the direction of the detector, can be deduced from the interference patterns recorded by the detector. The analysis of the interference patterns required to do so is performed like the analysis of the invisible laser radiation described in EP 2796938. Different colors may thus be assigned to different object points. For example, teeth and gums in the oral cavity can be differentiated from one another by color. In comparison with the analysis described in EP 2796938, no depth information is obtained from the interference patterns of the colored laser radiation in the present case. This simplifies the analysis.

The apparatus according to this disclosure may optionally also be used to recognize again object colors that are already known. This is done by performing a first reference measurement on a reference object with a known object color. The intensity determined for the reflected colored object radiation is measured and stored. Thus, in subsequent measurements, it is possible to check on the extent to which the object currently being measured contains this specific color component of the reference object by comparing the stored intensity value with the newly detected intensity value in subsequent measurements. It is thus also possible to differentiate regions of different color within an object even if only one color laser is present.

Color values of a color scale, in particular the Vita Color Scale, may also be used as reference objects. If the apparatus is used as a dental scanner, for example, the color of a tooth can be matched with a color value of the Vita Color Scale. It is also conceivable to store the measured intensity values for all color values of the Vita Color Scale in a memory medium. These intensity values can then be compared with intensity values determined on a patient's teeth.

The laser emitters, which emit laser radiation in the invisible range, preferably emit laser radiation in the near-infrared range. These laser emitters are very widespread and can therefore be acquired inexpensively. Within the context of the present disclosure, the near-infrared range is understood to include wavelengths of 780 nm to 1400 nm. It is self-evident that laser emitters that emit laser radiation in the invisible range but outside of the near-infrared range may also be used. For example, the laser radiation may have wavelengths in the infrared range, i.e., wavelengths of 1400 nm to 15,000 nm.

Optionally at least one color laser emits laser radiation with one of the primary colors. Within the context of this disclosure, the term "primary colors" includes the colors red, green and blue, such as those used for the RGB color space. Any color can be represented by mixing the three primary colors (red, green and blue). Conversely, this means that at least one of the primary colors is present in any color. If a color laser emits laser radiation with a primary color, then at least this primary color can be detected in the object to be measured. Within the context of this disclosure, the color blue is understood to refer to radiation with a wavelength of approximately 400 nm to 470 nm, the color green is understood to refer to radiation with a wavelength of approximately 500 nm to 580 nm and the color red is understood to refer to radiation with a wavelength of approximately 600 nm to 670 nm.

Especially preferred is an embodiment in which the at least one color laser emits blue light or green light. Optionally, in addition to the intensities of the object radiation of the color laser reflected on the object, the intensities of the object radiation of a laser emitter emitting in the near-infrared range are also used to deduce the color of the object to be detected. Laser emitters that emit laser radiation in the near-infrared range may be used to determine the color of the object to be detected because the laser radiation includes a red component. To this extent, a laser source that emits laser radiation in the near infrared may be used as a substitute for a color laser that emits red light.

By using a color laser that emits blue light together with a laser emitter that emits laser radiation in the near-infrared range, the edges of the color spectrum (blue to red) can thus be detected. If a color laser with green laser radiation is used additionally, then approximately the entire color spectrum between the colors blue and red can be detected. However, using a single color laser in combination with a laser emitter from the near infrared does not permit an unambiguous determination of the object color. It is then nevertheless possible on the basis of the color components contained (blue and green respectively, and red) to deduce the color composition of the object color, which is fundamentally already known. If the apparatus is used for detecting teeth and gingiva, for example, i.e., in a patient's oral cavity, then it is possible to differentiate between the whitish color of the teeth and the reddish color of the gingiva. Since the color white has a certain blue component, the whiteness of the teeth can be detected with the help of a blue color laser. The red component of the gingiva can be deduced by means of the red component of the laser emitter in the near-infrared range.

The apparatus advantageously includes at least four laser emitters, wherein at least two laser emitters are designed as color lasers and wherein one color laser emits blue light and the other color laser emits green light. If a laser emitter that emits laser radiation in the near-infrared range is used as a substitute for a red light, then a specific color determination of the object color is possible. Laser radiation of all primary colors of the RGB color space may be directed at the object to be detected. On the basis of the intensity of the reflected object radiation, the composition of the color of the object to be measured can thus be determined—in addition to the determination of the three-dimensional position and design—and thus the object color can be deduced.

An embodiment in which the apparatus comprises at least five laser emitters is particularly advantageous, wherein at least three laser emitters are designed as color lasers and wherein a first color laser emits blue light, a second color laser emits green light and a third color laser emits red light. A selected number of such color lasers and laser emitters respectively permit an unambiguous identification of the object color. A very high precision with which the object color can be determined is thus possible.

It is expedient that the apparatus comprises two emitter arrays, wherein the laser emitters that emit invisible laser radiation are preferably part of a first emitter array and preferably the at least one color laser is part of a second emitter array. The laser emitters of one array are preferably spaced a distance apart from one another in their arrangement on an emitter chip. Each laser emitter that emits invisible laser radiation emits laser radiation with a slightly different wavelength in comparison with its neighboring laser emitter. For example, the wavelengths of two neighboring laser emitters differ by 1 nm. Due to the arrangement of the laser emitters spaced a distance apart from one another, the reference radiation of the laser emitters strikes the detector at different angles. The illumination radiation also strikes the object to be detected at different incident angles. Therefore the individual interference patterns can be allocated to the respective laser emitters.

The at least one color laser in the second emitter array is particularly preferably arranged in a position which is conjugated with an unoccupied position in the first emitter array. These ambiguities in the analysis of the interference patterns are avoided. Within the context of the present disclosure, two positions are defined as conjugated if the laser radiation emitted from these positions is superimposed in the remaining course of the beam, i.e., the respective reference radiations are congruent and the respective illumination radiations are congruent. In the present case, one position in the first emitter array is conjugated with a position in the second emitter array when the emitted radiation is superimposed and coincides.

It is also conceivable that the position of a color laser in the second emitter array is arranged so that it is conjugated with a laser emitter in the first emitter array. In this case, the respective laser emitters must be controlled in such a way that either the color laser or the laser emitter in the first emitter array arranged so that it is conjugated therewith emits laser radiation. Only in this way can ambiguities in the analysis of the interference patterns be prevented. Therefore a position in the first emitter array is preferably empty when a color laser is arranged in the conjugated position in the second emitter array and this color laser emits or should emit colored laser radiation.

The apparatus optionally comprises an optical unit having four lenses and the beam splitter, wherein the lenses surround the beam splitter in a plane and wherein the two emitter arrays and the lenses are arranged in such a way that the reference radiation of the individual laser emitters leaves the optical unit in parallel and the illumination radiation of the individual laser emitters leaves the optical unit in parallel or essentially in parallel with one another. Due to the optical unit, it is possible to arrange the emitter arrays in different positions around the optical unit. For example, the four lenses may be arranged around the beam splitter in a quadratic arrangement and the emitter arrays may be positioned on two adjacent sides of this square. The two emitter arrays are thus preferably arranged at an angle of 90 degrees to one another.

Two lenses each of the optical unit are preferably arranged in parallel with one another and the beam splitter is positioned between these two lenses. The lenses are preferably all the same size and form the outside faces of a square. The beam splitter is preferably positioned at a 45-degree angle, i.e., as the diagonal in this square. Laser radiation passing through a lens along the optical axis thereof and being reflected by the beam splitter thus strikes a lens, which is offset by 90 degrees from the entrance lens, along the optical axis.

The apparatus advantageously comprises a microlens array, which comprises a plurality of lenses, preferably microlenses. The lenses may preferably be arranged in a plane. The microlens array can change the aperture of the illumination radiation. The microlens array is preferably designed so that the aperture of the illumination radiation can be altered so that the illumination radiation strikes the object in an illumination strip. For example, the illumination strip may have a rectangular shape, wherein the long side of the rectangle is preferably arranged transversely to a scanning direction of the apparatus, while the short sides of the rectangle are preferably positioned along the scanning direction. Within the context of the present disclosure, scanning direction is understood to be a direction of movement in which the apparatus according to this disclosure is moved, while it detects the 3D structure of an object. It is self-evident that the borders of the rectangular illumination strip are not absolutely sharp. According to the principles of optical wave propagation, fluid boundary regions have to be accepted.

The laser emitters and the lenses of the microlens array are preferably arranged in such a way that the illumination radiation of a laser emitter strikes a lens of the microlens array and passes through it. The radiation of the laser emitters preferably emitting in the near-infrared range preferably strikes the lens centrally, at any rate along the optical axis of the lens. The radiation is not deflected by the microlens array.

The illumination radiation strikes the microlens array and the individual lens respectively and passes through the array. The aperture of the illumination radiation is varied here along the scanning direction and the aperture across that, i.e., across the scanning direction, is also varied. The aperture along the scanning direction is preferably smaller than the aperture across it. Due to the use of at least one color laser, the illumination strip appears in color. The operator of the apparatus can thus recognize at all times which region of the object to be detected is currently being illuminated.

An embodiment in which the apparatus comprises a phase grating and a microlens array is particularly preferred. The phase grating splits the illumination radiation of the laser emitters that are emitting invisible laser radiation into two beams so that the illumination radiation preferably strikes the object in two illumination strips. The two illumination strips ensure that tilting of the apparatus relative to the object to be measured will not have a negative influence on the analysis of the interference patterns. By using at least two illumination strips, such tilting can be detected easily and corrected through calculations with the help of the analysis unit.

The phase grating is preferably designed so that the colored laser radiation passes through the phase grating almost unaffected. Within the context of the present disclosure, the phrase "almost without influence" is understood to mean that the components of the laser radiation being influenced by the phase grating are so low as to be of practically no relevance. In practical application it therefore does not have any negative effects on the evaluation of the interference patterns. The component is thus either negligible or can be eliminated through correction measures in the calculations. The phase grating is preferably designed and constructed so that it divides the incident laser radiation as a function of its wavelength. Laser radiation in the near-infrared with a wavelength of approximately 900 nm to 920 nm is split by the phase grating into two beams. Blue laser radiation with a wavelength of approximately 450 nm to 460 nm and green laser radiation with a wavelength of approximately 520 nm have a wavelength approximately half as large in comparison with laser radiation in the near-infrared range. Therefore, the blue laser radiation and green laser radiation are virtually unaffected in their passage through the phase grating. Blue laser radiation in particular, which has approximately half the wavelength of the radiation in the near-infrared range, is allowed to pass through the phase grating without diffraction and without any measurable deflection. Red laser radiation with a wavelength of approximately 600 nm also passes through the phase grating with a large undiffracted component. However, a small component of the red laser radiation is deflected by the phase grating. This component can be eliminated through the calculations in the subsequent analysis of the interference patterns. The smaller the difference between the wavelength of the colored laser radiation and the wavelength of the laser radiation in the near-infrared range, the greater is the component of the laser radiation deflected by the phase grating. Therefore, preferably max. two color lasers, which emit blue and/or green laser radiation, are used. The effects of the phase grating on the colored laser radiation can then be disregarded. At the same time, however, the color of the object to be measured is detected with a high accuracy.

Optionally the at least one color laser is positioned in such a way that the colored laser radiation strikes a lens of the microlens array outside of its optical axis so that the colored laser radiation is deflected by the lens. Various laser emitters, which emit invisible laser radiation, are preferably positioned in such a way that the illumination beams strike the lenses contained in the microlens array along their optical axes. The microlens array then alters only the aperture of the respective laser radiation but does not deflect it.

In the case of the colored laser radiation, however, a deflection is desirable because the phase grating does not influence the colored laser radiation because of its wavelength. Deflection of the colored laser radiation onto one of the two illumination strips therefore occurs in that the laser radiation strikes the respective lens of the microlens array eccentrically, not along (deviating from) the optical axis. The colored laser radiation is deflected with the help of the microlens array in such a manner that one of the illumination strips is colored. The colored radiation here is superimposed on the invisible radiation (e.g., infrared radiation) so the microlens array also alters the aperture of the colored laser radiation so that it fills up the entire rectangular area of the illumination strip.

The apparatus is preferably designed so that it can be used as a dental scanner and can be introduced into a patient's oral cavity. To meet these requirements, the apparatus preferably has corresponding dimensions, which permit at least partial insertion of the apparatus into the oral cavity. The optical system of the apparatus according to this disclosure therefore preferably has a diameter of max. 30 mm, especially preferably max. 20 mm. The optical system comprises the lens, by means of which the illumination radiation is parallelized and deflected onto the object and all additional optical devices, which are arranged between the lens and the object. The optical system preferably has a length of max. 150 mm, especially preferably max. 100 mm. The length of the optical system is defined as the distance between the abovementioned lens and the object-side end of the apparatus.

Part of this disclosure is also a use of the apparatus according to this disclosure as a dental scanner for detecting the tooth color according to a color scale, in particular the Vita Color Scale. The Vita Color Scale is a classification of tooth colors, similar to the RAL color chart in the graphics field that is widely used in the field of dentistry. Thus it is possible to accurately define the tooth color detected. For example, if a model is to be created, based on the three-dimensional structure of the tooth or the entire bite, the color of the tooth is defined unambiguously.

Part of this disclosure is also a method for detecting a 3D structure of an object and its color using the apparatus according to this disclosure. By means of at least two laser emitters, laser radiation in the invisible range is emitted. At least one additional laser emitter emits colored laser radiation. The laser radiation of the laser emitters is divided into a reference radiation and an illumination radiation. The illumination radiation strikes the object to be measured, is reflected by this object as object radiation and interferes with the reference radiation. The interference patterns formed due to the interference of the reference radiation and the object radiation are recorded by the detector. The object is detected in three dimensions with the help of the analysis unit, based on the interference patterns of the invisible laser radiation. On the basis of the intensity of the colored object radiation reflected by the object, the color of the object is deduced with the help of the analysis unit. Reliable detection of the color of an object is possible with the help of the method according to this disclosure.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
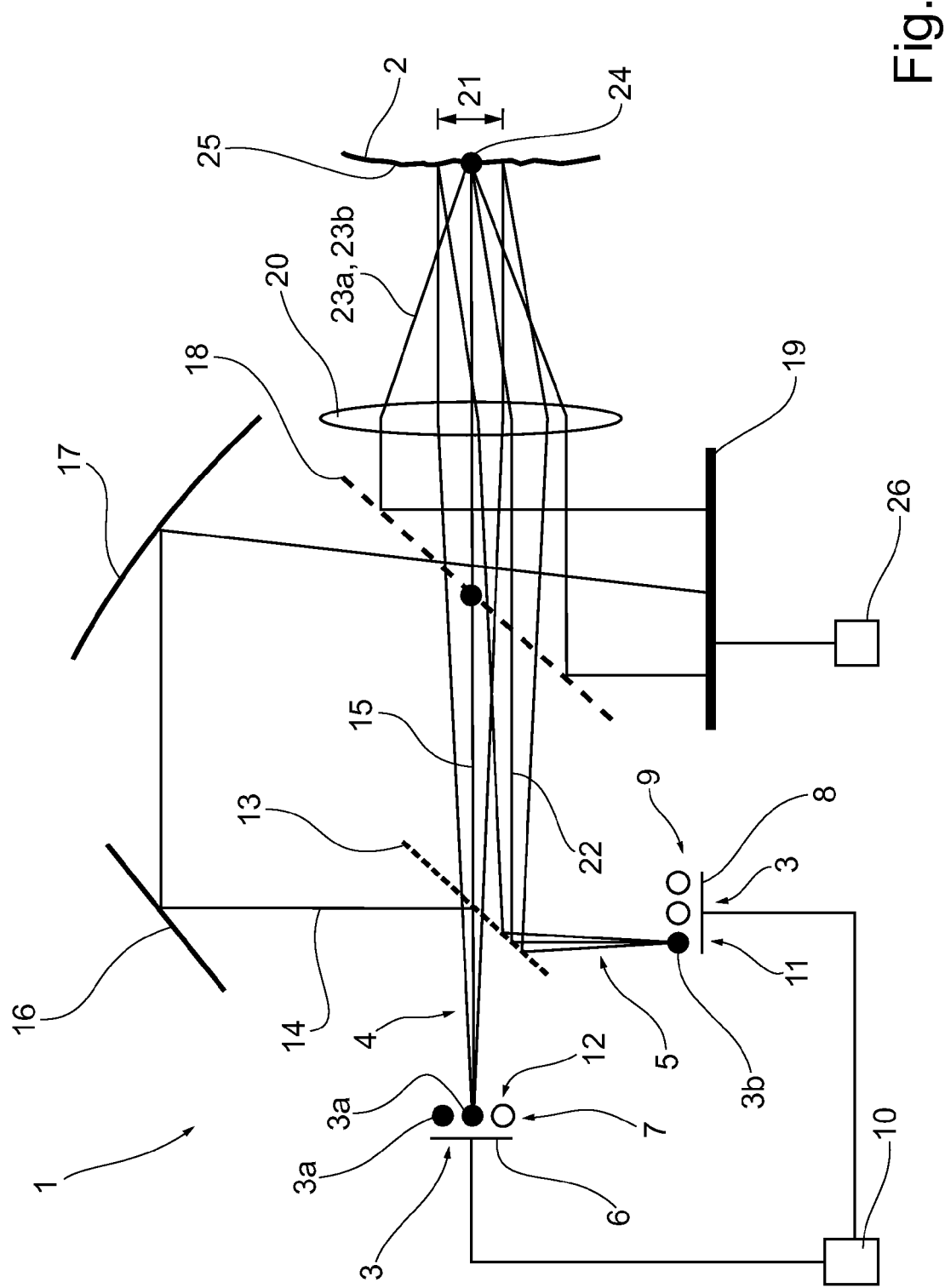
FIG. 1 shows an apparatus according to this disclosure in a first embodiment in a Mach-Zehnder design, shown schematically.

FIG. 1 shows a first embodiment of an apparatus 1 for detecting a 3D structure of an object 2 in a Mach-Zehnder design. The apparatus 1 comprises three laser emitters 3, two of which are designed as laser emitters 3a, which emit invisible laser radiation 4 in the near-infrared range with a wavelength of approximately 900 nm. Each of the two laser emitters 3a emits laser radiation 4 at a different wavelength. The wavelengths of the laser radiation 4 of two neighboring laser emitters 3a preferably differ only slightly by 1 nm, for example. The third laser emitter is designed as a color laser 3b, which preferably emits blue laser radiation 5 with a wavelength of approximately 460 nm, for example.

Whereas the laser emitters 3a are arranged on a first emitter chip 6 and are part of a first emitter array 7, the color laser 3b is preferably arranged on a second emitter chip 8 and is part of a second emitter array 9.

The laser emitters 3 of both emitter arrays 7, 9 and both emitter chips 6, 8 respectively are connected to a control unit 10. With the help of the control unit 10 the laser emitters 3 can be controlled individually, for example, being turned on and off individually.

The color laser 3b is preferably positioned in a position 11 on the second emitter chip 8, which is conjugated in relation to a position 12 on the first emitter chip 6. Preferably no laser emitter 3 is arranged in position 12. However, if a laser emitter 3 should be arranged in position 12, then it is not turned on and does not emit any laser radiation.

Within the context of the present disclosure, two different positions (positions 11 and 12 here) may be defined as conjugated if laser radiation emitted by these positions is superimposed, i.e., congruent in the remaining course of the beam. In the present case, the laser radiation 5 of the color laser 3b (in position 11), after being reflected on an optical unit embodied as a beam splitter 13, would be coincident with the laser radiation of a laser emitter that is not shown here in position 12 after this laser radiation has been transmitted through the beam splitter 13.

The path of the beam of the laser radiation 4 of one of the laser emitters 3a as well as the course of the beam of the laser radiation 5 of the color laser 3b is to be explained in greater detail below as examples of the laser radiation used.

The laser radiation 4 is emitted by one of the laser emitters 3a and strikes the beam splitter 13. The beam splitter 13 splits the laser radiation 4 into a reference radiation 14 and an illumination radiation 15. The reference radiation 14 is the portion of the laser radiation 4 reflected on the beam splitter 13. It is deflected onto a second beam splitter 18 in the remaining course by means of two mirrors, preferably one mirror 16 and one parabolic mirror 17. The reference radiation passes through the second beam splitter 18 and strikes a detector 19.

The illumination radiation 15 is the portion of the laser radiation 4 that is transmitted through the beam splitter 13. In the remaining course, the illumination radiation 15 also penetrates through the second beam splitter 18 and strikes a lens 20, for example, which parallelizes the illumination beams and deflects them onto the object 2. The lens 20 deflects the illumination radiation 15 in such a way that it preferentially strikes the object 2 in a rectangular illumination strip 21. "Rectangular" in this context does not mean that the illuminated borders are absolutely sharp. According to the principles of optical wave propagation, fluid boundary regions must instead be accepted.

The laser radiation 5 of the color laser 3b is also preferably split by the beam splitter 13 into reference radiation (not shown) and illumination radiation 22. The reference radiation of the color laser 3b runs as far as the detector 19, like the reference radiation 14 of the laser emitter 3a. The illumination radiation 22 of the color laser 3b is formed by reflection of the laser radiation 5 on the beam splitter 13. In the remaining course, it passes through the second beam splitter 18 and strikes the lens 20. The lens 20 parallelizes the laser radiation 22 and deflects it in such a way that it preferentially strikes the object 2 as illumination beam 21.

The illumination radiation 15 of the laser emitter 3a is reflected as object radiation 23a on the object 2. The illumination radiation 22 of the color laser 3b is reflected as object radiation 23b on the object 2. The path of the object radiation 23a, 23b will now be exemplified for one object point 24 on a surface 25 of the object 2. The object radiations 23a, 23b emanating from the object point 24 thus coincide. It is self-evident that the surface 25 has a finite number of object points, all of which are capable of reflecting the illumination radiation 15, 22 of the laser emitters 3 as object radiation 23a, 23b.

For an understanding of the beam paths the object point 24 can be regarded in simplified terms as a point light source. The point light source emits object radiation 23a, 23b that strikes the lens 20, is preferably parallelized by it and strikes the second beam splitter 18. The object radiation 23a, 23b is reflected on the second beam splitter 18 and then reaches detector 19.

The reference radiation 14 and the object radiation 23a of one of the laser emitters 3a, i.e., laser radiation of the same wavelength cause interference with one another on the detector 19. This interference causes an interference pattern of a certain spatial frequency that is recorded.

For all laser emitters 3a, such an interference pattern is recorded by the detector 19. On the basis of these interference patterns, depth information about the surface 25 of the object 2 can be obtained and thus the structure of the surface 25 can be ascertained. The detector 19 is therefore connected to an analysis unit 26, which performs the analysis of the interference patterns.

The analysis unit 26 is designed to detect the object 2 in three dimensions, based on the interference patterns of the invisible laser radiation 4. For a detailed explanation of the beam path of the laser radiation 4 and for a detailed explanation of the evaluation of the interference patterns, reference is made to EP 2796938 to the full extent.

The object radiation 23b of the color laser 3b and the respective reference radiation (not shown) also interfere on the detector 19. The resulting interference patterns are evaluated with the help of the analysis unit 26. The goal of this analysis is to determine the lateral position of the object point 24 on which the object radiation 23b of the color laser 3b was reflected towards the detector 19. The lateral position of the object point 24 is understood within the context of the present disclosure to refer to the position of the object point 24 in the vertical direction in the image plane in FIG. 1 and transverse to the image plane. The depth information, i.e., the position of the object point 24 in the horizontal direction in the image plane in FIG. 1 cannot be obtained by analysis of the interference patterns of the colored laser radiation 5. To avoid ambiguities in the analysis of the interference patterns, the color lasers 3b are preferably arranged so that they are not conjugated with the laser emitters 3a, which emit laser radiation 4 from the near-infrared range.

In addition, the analysis unit 26 is designed to ascertain the intensity of the colored object radiation 23b reflected by the object 2. On the basis of the intensity, the color of the object 2 can preferably be deduced by means of the analysis unit 26. This will be explained below:

If the apparatus 1 is used as a dental scanner as in the present case, then a distinction must be made between teeth having a white color or approximately white color and gingiva having a red color.

On the basis of the intensity of the blue object radiation 23b of the color laser 3b reflected by the object 2, the amount of blue color in the color of the object 2 can be ascertained. Since the color white has a certain blue component, the color of the teeth can be detected with the help of the blue laser radiation of the color laser 3b.

To detect the red coloration of the gingiva, the intensity of the object radiation 23a of one of the laser emitters 3a is additionally analyzed. Since the laser emitters 3a emit laser radiation 4 in the near-infrared, i.e., with a wavelength of approximately 900 nm, the laser radiation 4 has a red component. On the basis of the intensity of the object radiation 23a of the laser emitters 3a reflected by the object 2, it is thus possible to ascertain the amount of red color in the color of object 2.

The information about which color information (white or red) is to be allocated to which object point 24 of the object 2 to be detected, is obtained on the basis of the interference patterns formed by the laser radiation 5 of the color laser 3d and by the laser radiation 4 of the laser emitters 3a with the help of the analysis unit 26. A more detailed determination of the individual color components of an object may be made by means of reference measurements. If the colors to be detected are known or can be determined in advance, reference measurements for these colors can be performed. The actual measurements then lead to better measurement results because certain color components can be inferred by means of the reference measurements. In a preferred embodiment, the apparatus therefore includes a data memory or a memory unit, in which the reference data of the reference measurements is preferably stored. Reference measurements can be performed with different hues of a color scale, in particular with the Vita Color Scale, for example. Then the color of an object, for example, a tooth, can be matched with the exact hue of the Vita Color Scale by means of the analysis unit 26.

It is self-evident that this disclosure is not fixated on the number of one color laser 3b. Instead, it is possible to use up to three color lasers 3b, which emit laser radiation with the three primary colors (blue, green and red). All colors are made up of these three primary colors, which is why any object color can be ascertained unambiguously with the help of the three color lasers 3b. It is self-evident that more than three color lasers 3b may also be provided, in which case the same primary color is then emitted by multiple lasers. It is also conceivable to use primary colors other than those above (red, green, blue), for example, cyan, magenta and yellow (CMY standard).

The number of laser emitters 3a emitting laser radiation 4 in the near-infrared range is not limited to two laser emitters 3a. Definitely more than two laser emitters 3a may be used in the apparatus 1. At any rate, however, at least two laser emitters 3a are necessary to detect the object 2 in three dimensions.

On the whole, for example, four laser emitters 3 may be used, at least two laser emitters being embodied as color lasers 3b and preferably one color laser emitting blue light and the other color laser emitting green light. Alternatively, it is also possible for the apparatus to comprise as least five laser emitters 3, at least three laser emitters being designed as color lasers 3b and a first color laser emitting blue light, a second color laser emitting green light and a third color laser emitting red light. At any rate, at least two laser emitters 3a are necessary in this preferred embodiment to detect the object 2 in three dimensions.

Figure 2:
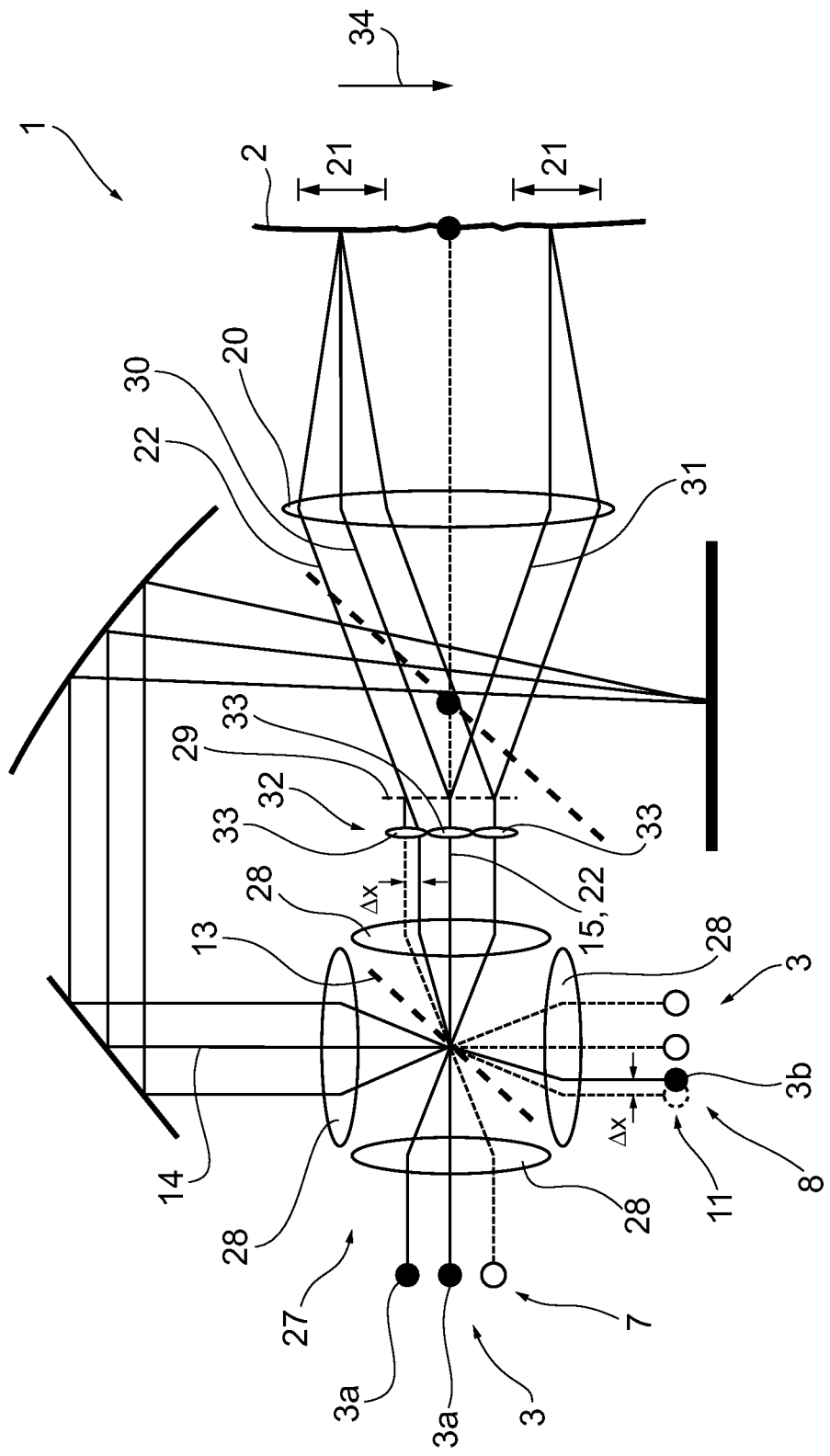
FIG. 2 shows the apparatus according to this disclosure in a second embodiment having an optical unit and two illumination strips, in a schematic diagram.

FIG. 2 shows a preferred second embodiment of the apparatus 1. The apparatus 1 differs from the first embodiment according to FIG. 1 in an optical unit 27. The optical unit 27 has four lenses 28 and the beam splitter 13, wherein the lenses 28 preferably surround the beam splitter 13 in a plane. Two opposing lenses 28 each are arranged parallel to one another, the beam splitter 13 being positioned between these two lenses 28. On the whole, the lenses 28 preferably form side faces of a square or a rectangle or a quadrilateral whose diagonal is formed by the beam splitter 13.

The two emitter arrays 7, 8, i.e., the laser emitter 3a and also the color laser 3b are arranged on side faces of the optical unit 27 in such a way that the reference radiation 14 of the individual laser emitters 3 leave the optical unit 27 in parallel with one another. The illumination radiation 15, 22 of the individual laser emitters 3 also leaves the optical unit 27 in parallel to one another.

The apparatus 1 according to FIG. 2 also differs more preferably in the phase grating 29, which splits the illumination radiation 15 of each laser emitter 3a into two beams. The division into a first beam 30 and a second beam 31 causes the illumination radiation 15 to strike the object 2 in two illumination strips 21. The phase grating 29 is designed, so that the colored illumination radiation 22 passes through the phase grating 29 without being influenced. The effect of the phase grating 29 on the illumination radiation 15, 22 takes place as a function of the wavelength of the illumination radiation 15, 22. The phase grating 29 splits radiation of a certain wavelength and allows radiation of a different wavelength to pass through unhindered. The laser radiation 4 with a wavelength of approximately 900 nm is split into the beams 30, 31 while the influence of the colored laser radiation is mirror due to the phase grating. In the case of laser radiation with a wavelength of 460 nm (blue) the influence cannot be detected. In the case of radiation with a wavelength of 520 nm (green), the influence is negligible and has no practical effects on the measurement. Red laser radiation with a wavelength of 600 nm is influenced to such a minor extent that the influence can be compensated easily by calculation and therefore is of no practical relevance here.

After passing through the phase grating 29, the beams 30, 31 strike the lens 20, which parallelizes the illumination radiation 15 as in the embodiment in FIG. 1. In contrast with FIG. 1, only the central rays of the illumination radiation 15 are shown for reasons of simplicity, so that the illumination strips 21 also appear as illumination points. The course of the object radiation 23a, 23b is similar to that described with reference to FIG. 1.

In the direction of the path of the beam upstream from the phase grating 29 microlens array 32 comprising a plurality of microlenses 33 is arranged. The microlens array 32 is designed to alter the aperture of the illumination radiation 15, 22 in such a way that the illumination radiation 15, 22 strikes the object 2 in a rectangular illumination strip. The illumination aperture along a scanning direction 34 along which the apparatus 1 for detecting the object 2 is moved is smaller than the aperture across the scanning direction 34. This results in illumination strips 21, which are shorter along the scanning direction 34 than across the scanning direction 34.

In addition, the microlens array 32 is designed to deflect the colored laser radiation 5, in particular the illumination radiation 22 of the color laser 3b in such a manner that preferably one of the illumination strips 21 is colored. This is the illumination strip 21 at the top of FIG. 2.

The color laser 3b is therefore arranged so that it is displaced by the distance Ax from the conjugated position 11 in contrast with FIG. 1. The laser radiation 5, after being reflected on the first beam splitter 13, therefore strikes one of the lenses 33 of the microlens array 32 eccentrically, offset by the distance $\Delta x$. The illumination radiation 22 is therefore preferably deflected toward the optical axis of the microlens array 32. In doing so, the illumination radiation 22 deflected by the microlens array 32 runs parallel to the two beams 30, 31 of the laser emitters 3a, these beams being split by the phase grating 29.

FIG. 2 shows the conjugated position 11 and the resulting beam path of the laser radiation 5 with broken lines. The position of the color laser 3b that has been deflected (shifted) by $\Delta x$ and the actual beam path of the laser radiation 5 are represented by the solid line in FIG. 2.

The color laser 3b is thus positioned in such a way that the colored laser radiation 5, in particular the illumination radiation 22, strikes a lens of the microlens array 32 outside of its optical axis so that the colored laser radiation 5 is deflected by the lens. However, in the remaining course there is no deflection of the colored laser radiation 5 by the phase grating 29. The shift in the position of the color laser 3b in the second emitter array 9 is preferably so large that the illumination radiation 22 is parallel, for example, to the first illumination radiation 30 between the phase grating 29 and the lens 20. This ensures that the illumination radiation 22 deflected in the lens 20 strikes the illumination strip 21 and/or, as shown here, strikes the illumination point 21 with the radiation from the laser emitters 3a.

The distance between the microlens array 32 and the phase grating 29 is preferably selected so that the colored illumination radiation 22 striking the lens 33 of the microlens array 32, so that it is offset eccentrically, is deflected toward the optical axis of the lens so that the deflected radiation intersects the optical axis of the lens 33 in the plane of the phase grating 29.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. An apparatus for detecting a 3D structure of an object, comprising:
   at least three laser emitters, each of which emits laser radiation at a different wavelength;
   optical devices, including a beam splitter that splits the laser radiation of the laser emitters into a reference radiation and an illumination radiation, wherein the illumination radiation is adapted to strike the object to be measured, to be reflected by the object as object radiation, and to interfere with the reference radiation;
   a detector adapted to receive the interference patterns formed due to the interference of the reference radiation and the object radiation; and
   an analysis unit connected to the detector, the analysis unit configured for analyzing the recorded interference patterns;
   wherein at least two of the laser emitters emit laser radiation in the invisible range of between about 780 nm to about 15,000 nm, and wherein the analysis unit is configured to detect the object in three dimensions based on the interference patterns of the invisible laser radiation;
   further wherein at least one of the laser emitters is a color laser that emits colored laser radiation and the analysis unit is configured to deduce the color of the object based on the intensity of the colored object radiation reflected by the object.

2. The apparatus according to claim 1, wherein the at least one color laser emits laser radiation with one of the primary colors.

3. The apparatus according to claim 1, wherein the at least one color laser emits blue light or green light.

4. The apparatus according to claim 1, wherein the apparatus comprises at least four laser emitters, wherein at least two laser emitters are color lasers, and wherein one of the color lasers emits blue light and the other color laser emits green light.

5. The apparatus according to claim 1, wherein the apparatus comprises at least five laser emitters, wherein at least three of the laser emitters are color lasers, and wherein a first one of the color lasers emits blue light, a second one of the color lasers emits green light and the third color laser emits red light.

6. The apparatus according to claim 1, wherein the apparatus comprises first and second emitter arrays, wherein the laser emitters that emit invisible laser radiation are part of the first emitter array and the at least one color laser is part of the second emitter array.

7. The apparatus according to claim 6, wherein the at least one color laser is arranged in a position in the second emitter array, which is conjugated with an unoccupied position for a laser emitter or with a non-emitting laser emitter in the first emitter array.

8. The apparatus according to claim 6, wherein the apparatus comprises an optical unit having four lenses and the beam splitter, wherein the lenses surround the beam splitter in one plane, and wherein the two emitter arrays and the lenses are arranged such that the reference radiation of the individual laser emitters leave the optical unit in parallel with one another, and the illumination radiation of the individual laser emitters leave the optical unit in parallel with one another.

9. The apparatus according to claim 1, wherein the apparatus comprises a microlens array configured to alter the aperture of the illumination radiation such that the illumination radiation strikes the object in an illumination strip.

10. The apparatus according to claim 1, further comprising:
    a phase grating, which splits the illumination radiation of the laser emitters that emit invisible laser radiation into two beams so that the illumination radiation strikes the object in two illumination strips; and
    a microlens array, which deflects the colored laser radiation of the at least one color laser through the microlens array such that one of the illumination strips is colored.

11. The apparatus according to claim 10, wherein the phase grating is configured such that the colored laser radiation passes through the phase grating without substantially being influenced.

12. The apparatus according to claim 10, wherein the at least one color laser is positioned such that the colored laser radiation strikes a lens of the microlens array outside of the optical axis thereof so that the colored laser radiation is deflected by the lens.

13. The apparatus according to claim 1, wherein the apparatus is configured for use as a dental scanner that can be introduced into a patient's oral cavity.

14. A method for detecting a 3D structure of an object and its color using an apparatus having at least three laser emitters, a beam splitter, a detector and an analysis unit, the method comprising:
    emitting laser radiation in the invisible range of between about 780 nm to about 15,000 nm with at least two laser emitters and emitting colored laser radiation with at least one additional laser emitter;
    splitting the laser radiation of the laser emitters into a reference radiation and an illumination radiation;
    striking an object to be measured with the illumination radiation, reflecting the radiation from the object as object radiation, and forming an interference of the object radiation and the reference radiation;
    recording with the detector the interference patterns formed due to the interference of the reference radiation and the object radiation;
    using the analysis unit to detect the object in three dimensions based on the interference patterns of the invisible laser radiation; and
    using the analysis unit to deduce the color of the object based on the intensity of the colored object radiation reflected by the object.

15. The method according to claim 14, comprising detecting tooth color according to a color scale.

16. The method of claim 15, wherein the color scale is the Vita Color Scale.

* * * * *